United States Patent [19]

Martin

[11] 3,986,026

[45] Oct. 12, 1976

[54] APPARATUS FOR PROTON RADIOGRAPHY

[75] Inventor: Ronald L. Martin, La Grange, Ill.

[73] Assignee: The United States of America as represented by the United States Energy Research and Development Administration, Washington, D.C.

[22] Filed: Nov. 14, 1975

[21] Appl. No.: 632,030

[52] U.S. Cl. .......................... 250/306; 250/358 R; 328/235
[51] Int. Cl.² ........................................ G01N 23/02
[58] Field of Search ............... 250/306, 307, 358 R; 313/359, 363; 328/235

[56] References Cited
UNITED STATES PATENTS

| | | | |
|---|---|---|---|
| 3,139,591 | 6/1964 | Rheaume et al. | 328/235 X |
| 3,370,167 | 2/1968 | Sterk | 250/306 |
| 3,576,997 | 5/1971 | Slavin | 250/490 X |

OTHER PUBLICATIONS

Proton Radiography in Tumor Detection, by Steward et al., from Science, vol. 179 (1973), pp. 913, 914.

*Primary Examiner*—Archie R. Borchelt
*Attorney, Agent, or Firm*—Dean E. Carlson; Arthur A. Churm; Donald P. Reynolds

[57] ABSTRACT

An apparatus for effecting diagnostic proton radiography of patients in hospitals comprises a source of negative hydrogen ions, a synchrotron for accelerating the negative hydrogen ions to a predetermined energy, a plurality of stations for stripping extraction of a radiography beam of protons, means for sweeping the extracted beam to cover a target, and means for measuring the residual range, residual energy, or percentage transmission of protons that pass through the target. The combination of information identifying the position of the beam with information about particles traversing the subject and the back absorber is performed with the aid of a computer to provide a proton radiograph of the subject. In an alternate embodiment of the invention, a back absorber comprises a plurality of scintillators which are coupled to detectors.

10 Claims, 7 Drawing Figures

| 34 | 28 | 23 | 19 | 17 | 18 | 6  | 1  | 8  | 19 | 16 | 17 | 18 | 21 | 33 | 44 | 43 | 40 | 37 | 29 | 23 | 17 |
|----|----|----|----|----|----|----|----|----|----|----|----|----|----|----|----|----|----|----|----|----|----|
| 37 | 30 | 20 | 16 | 15 | 13 | 13 | 13 | 15 | 16 | 15 | 15 | 18 | 31 | 45 | 46 | 45 | 41 | 36 | 33 | 26 | 18 |
| 38 | 30 | 18 | 14 | 10 | 9  | 11 | 10 | 10 | 11 | 12 | 13 | 19 | 37 | 47 | 46 | 44 | 40 | 38 | 33 | 30 | 21 |
| 37 | 29 | 18 | 13 | 9  | 8  | 8  | 8  | 8  | 9  | 12 | 19 | 26 | 35 | 43 | 46 | 43 | 38 | 38 | 37 | 34 | 24 |
| 36 | 27 | 17 | 14 | 9  | 8  | 9  | 11 | 12 | 15 | 20 | 25 | 29 | 34 | 40 | 44 | 42 | 39 | 38 | 39 | 34 | 21 |
| 40 | 30 | 21 | 14 | 12 | 12 | 14 | 15 | 18 | 21 | 24 | 26 | 28 | 31 | 37 | 44 | 40 | 38 | 38 | 39 | 34 | 25 |
| 47 | 42 | 35 | 27 | 21 | 20 | 22 | 22 | 24 | 26 | 26 | 27 | 27 | 29 | 32 | 38 | 38 | 35 | 38 | 38 | 33 | 23 |
| 45 | 44 | 36 | 33 | 32 | 31 | 29 | 26 | 26 | 25 | 24 | 24 | 26 | 29 | 33 | 37 | 36 | 35 | 38 | 38 | 34 | 23 |
| 43 | 44 | 40 | 34 | 33 | 30 | 30 | 28 | 27 | 26 | 25 | 24 | 25 | 27 | 33 | 36 | 35 | 35 | 38 | 37 | 31 | 31 |
| 40 | 43 | 46 | 39 | 35 | 35 | 36 | 35 | 34 | 32 | 30 | 28 | 28 | 31 | 35 | 33 | 32 | 36 | 38 | 35 | 30 | 19 |
| 37 | 37 | 39 | 39 | 37 | 35 | 34 | 37 | 38 | 34 | 30 | 28 | 31 | 31 | 26 | 26 | 32 | 38 | 39 | 36 | 30 | 18 |
| 37 | 34 | 28 | 29 | 29 | 33 | 34 | 33 | 32 | 32 | 28 | 27 | 26 | 22 | 21 | 30 | 35 | 38 | 37 | 34 | 25 | 15 |
| 44 | 43 | 37 | 33 | 29 | 29 | 36 | 36 | 33 | 31 | 26 | 26 | 25 | 22 | 28 | 37 | 39 | 40 | 36 | 30 | 18 | 15 |
| 42 | 43 | 41 | 33 | 30 | 30 | 32 | 33 | 30 | 27 | 24 | 23 | 22 | 24 | 33 | 37 | 36 | 35 | 29 | 21 | 17 | 17 |
| 39 | 41 | 41 | 38 | 39 | 38 | 33 | 31 | 32 | 32 | 29 | 27 | 28 | 34 | 37 | 39 | 35 | 30 | 21 | 16 | 18 | 18 |
| 31 | 36 | 38 | 39 | 40 | 38 | 37 | 38 | 39 | 37 | 31 | 29 | 28 | 31 | 32 | 31 | 25 | 17 | 16 | 19 | 20 | 18 |
| 17 | 20 | 26 | 30 | 30 | 31 | 31 | 32 | 31 | 30 | 25 | 21 | 16 | 18 | 20 | 17 | 14 | 16 | 17 | 18 | 18 | 16 |
| 18 | 18 | 17 | 18 | 19 | 22 | 22 | 22 | 22 | 20 | 19 | 17 | 14 | 11 | 13 | 16 | 17 | 17 | 17 | 18 | 18 | 15 |
| 17 | 17 | 19 | 17 | 16 | 17 | 18 | 15 | 15 | 16 | 16 | 16 | 15 | 15 | 16 | 16 | 16 | 16 | 15 | 16 | 16 | 14 |

FIG—5

APPARATUS FOR PROTON RADIOGRAPHY

CONTRACTUAL ORIGIN OF THE INVENTION

The invention described herein was made in the course of, or under, a contract with the UNITED STATES ENERGY RESEARCH AND DEVELOPMENT ADMINISTRATION.

BACKGROUND OF THE INVENTION

This invention relates to proton radiography of human subjects.

Diagnostic radiologists are constantly seeking more useful radiographs and other means for internal visualization that minimize the risk of harm to patients. The detection by X-rays of anomalies such as cancers and other tumors is rendered more difficult by the fact that X-rays produce an image by absorption in material through which they pass. This absorption is proportional to the square of the atomic number of the material in the path of the X-rays. Thus, bones, largely calcium, are easy to distinguish and soft tissue, mostly carbon, hydrogen, and oxygen, is not. In particular, cancerous lesions have very nearly the same atomic composition as normal cells. Visualization of such lesions has therefore been accomplished by injection or ingestion of a material of high atomic number which will concentrate in the lesion to increase its opacity to X-rays. A similar means of visualizing lesions in certain parts of the human body involves the administration of compounds containing radioisotopes that are taken up preferentially by the lesions. Each of these means, administration of dense compounds and administration of radioactive compounds, presents a potential threat to the well-being of the patient that would be better avoided if possible.

It is known that one way to avoid the threats outlined above is to expose the suspected lesion to a flux of ions. It is possible to detect differences in the energy loss in a beam of ions when the beam is passed through a substance. This energy loss is proportional to density, and in particular electron density. If a lesions exhibits a difference in density from the surrounding material, this density difference may be detected to provide a picture of the lesion which would be difficult or impossible to attain using X-rays. Other advantages exist from the use of ion beams, particularly beams of protons. Since no tracer or radiopaque material need be administered, there is no problem of delay in obtaining pictures resulting from the time necessary to ingest and distribute such tracer or radiopaque material. In addition, it has proved possible to obtain proton radiographs using extremely low levels of radiation.

The conclusions stated above have resulted from investigative work that has been carried out at various Accelerator Laboratories. Each such study has involved using an accelerator designed for research in high-energy physics in a manner for which the accelerator is marginally adapted. Relative to the needs of diagnostic proton radiography, the particle-research accelerators are expensive to build and complicated and expensive to operate. They produce too many protons in a beam whose particle density across a cross section is too high. The beam they produce is not designed either to be swept or to be defocused into a uniformly diffuse beam. Finally, and this is a serious disadvantage, they are not located in or conveniently near hospitals. The combination of factors outlined above suggests a need for a proton diagnostic accelerator that is sufficiently inexpensive to build and simple to operate and that is sufficiently safe that it can be located and routinely operated in a hospital.

It is an object of the present invention to provide facilities for proton radiography for location in a hospital.

It is a further object of the present invention to provide means located in a hospital for obtaining diagnostic proton radiographs.

Other objects will become apparent in the course of a detailed description of the invention.

SUMMARY OF THE INVENTION

An apparatus for obtaining diagnostic proton radiographs of human patients in a hospital comprises a source of negative hydrogen ions, a synchrotron accelerator for accelerating the negative hydrogen ions to an energy of the order of 200 MeV with a small energy spread, a plurality of stripping stations for converting the negative hydrogen ions to positive hydrogen ions in beams of extremely high quality, means for sweeping each of the beams in a raster covering a desired area, means for detecting energy changes in the beam associated with soft tissue, and means for displaying these changes as a function of position to produce a proton radiograph of the soft tissue.

BRIEF DESCRIPTION OF THE DRAWINGS

FIG. 2 is an expanded view of the source and synchrotron of FIG. 1.

FIG. 3a is an alternate embodiment of the back absorber of FIG. 3.

DETAILED DESCRIPTION OF THE INVENTION

Figure 1:
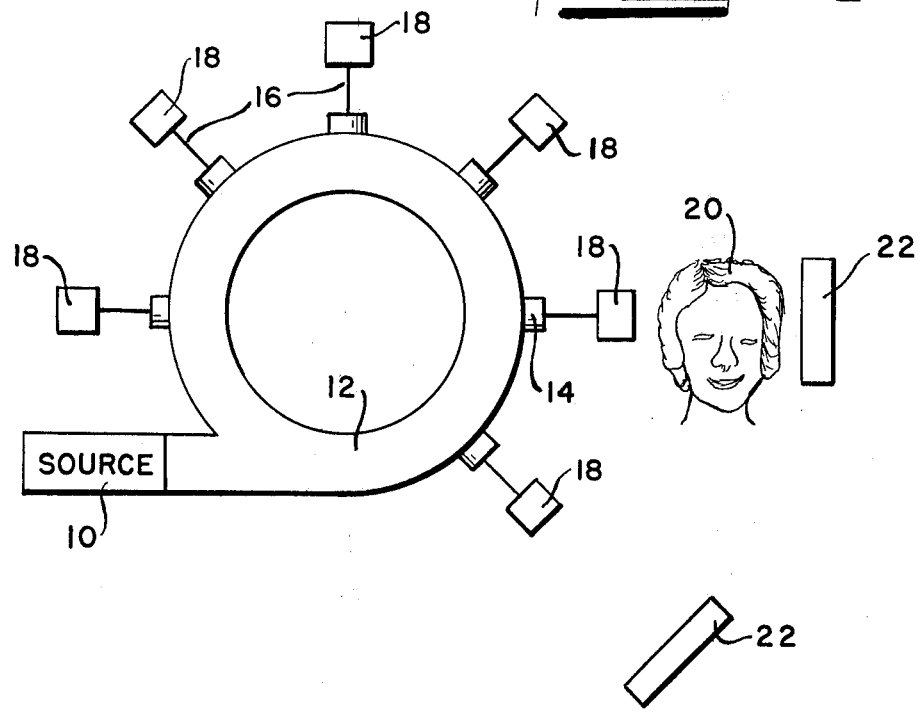
FIG. 1 is an overall schematic diagram of an apparatus for the practice of the present invention.

FIG. 1 is an overall sketch of an apparatus for the practice of the present invention. In FIG. 1 source 10 is a generator of negative hydrogen ions which are inserted into synchrotron 12 for acceleration to a desired controlled energy. Strippers 14 convert accelerated negative hydrogen ions to protons by removing the electrons therefrom. The proton beam 16 that results from stripping is caused by sweeping means 18 to execute a sweeping pattern or raster on subject 20. Detection and display means 22 respond to the protons that traverse subject 20 to produce therefrom a proton radiograph of subject 20. A plurality of strippers 14, sweeping means 18, and detection and display means 22 is shown in FIG. 1. In one application of the present invention a proton radiograph will be made of a subject by using one accelerated bunch of negative hydrogen ions that is extracted as protons and is swept over an interval of the order of one second. The plurality of strippers 14, sweeping means 18 and detection and display means 22 facilitates the placing and preparation of one or more patients while a radiogram is being obtained of a subject patient.

FIG. 2 is an expanded view of the synchrotron 12 of FIG. 1. In FIG. 2 source 10 generates negative hydrogen ions which are deflected for injection into synchrotron 12 by kicker magnet 30. Bending magnet 32 and focusing quadrupole magnet 33 combine to bend and focus the beam of negative hydrogen ions and are caused to receive appropriately changing magnetic fields so that as the beam undergoes acceleration from beam accelerator 34 the equilibrium radius of the beam remains substantially the same at about 12 or 13 feet. Thus, after a number of passages through beam accelerator 34, the magnetic field of bending magnet 32 will have been caused to rise to a magnetic field of the order of 6 to 8 kiloGauss (0.6–0.8 Tesla). At this point bumping magnet 35 is energized at a desired time to cause enough of a shift in the path of accelerated particles to place some of the particles in contact with stripper 36, a fixed foil stripper. This strips electrons to convert the negative hydrogen ions to protons which are then bent in the opposite direction by the next following bending magnet 32. Before the application of a bumping current to bumping magnet 35, the path of the accelerating and accelerated beams is alternately in vacuum straight sections 38 and vacuum curved sections 40. Vacuum straight sections 38 carry the beam in a straight path when it is not subject to the influence of a bending magnetic field. Vacuum curved sections 40 carry the beam in a path that is an arc of a circle when the path is subject to the centripetal acceleration associated with the velocity of a charged particle in a uniform magnetic field. Vacuum pumps 42 are connected to various vacuum straight sections 38 to maintain the extremely high vacuum that is needed for successful operation of such a synchrotron. This vacuum is of the order of $10^{-10}$ picoPascals or hundreds of picoTorrs to minimize scattering and unwanted stripping of the negative hydrogen ions during acceleration. The proton extraction is a part of the same vacuum system and comprises a section 44 that is curved in the opposite direction from vacuum curved section 40. This results from the fact that protons are charged oppositely from negative hydrogen ions and is the basis of the stripping extraction which is an essential feature of the present invention.

Beam accelerator 34 comprises an r-f accelerating gap having a peak voltage of the order of 100 volts at frequencies ranging from approximately 500 kHz to approximately 10 MHz. The frequency of the r-f excitation applied to beam accelerator 34 and the value of the magnetic field of bending magnet 32 are controlled together by controller 46 which maintains the radius of the accelerating and accelerated beam at a position which keeps it within the vacuum system. In maintaining this control of the position of the beam so that the beam remains within the vacuum straight sections 38 and the vacuum curved sections 40 bending magnets 32 may be constructed as conventional magnets for alternating-gradient synchrotrons, with gaps on adjacent magnet sections being beveled to place the gradient of the magnetic field alternately inward and outward and thus accomplish focusing together with bending. In the alternative, bending magnets 32 may be constructed to produce a zero gradient of the magnetic field with focusing supplied by a focusing quadrupole magnet 33 of which there may be several in different locations. These are alternatives for choice by the accelerator designer. The least expensive design is expected to result from using the conventional bevel to create nonuniform gaps in bending magnets 32 and hence to construct a combined-function alternating-gradient synchrotron. This is in contrast to the separated-function alternating-gradient synchrotron that uses focusing quadrupoles.

Figure 3:
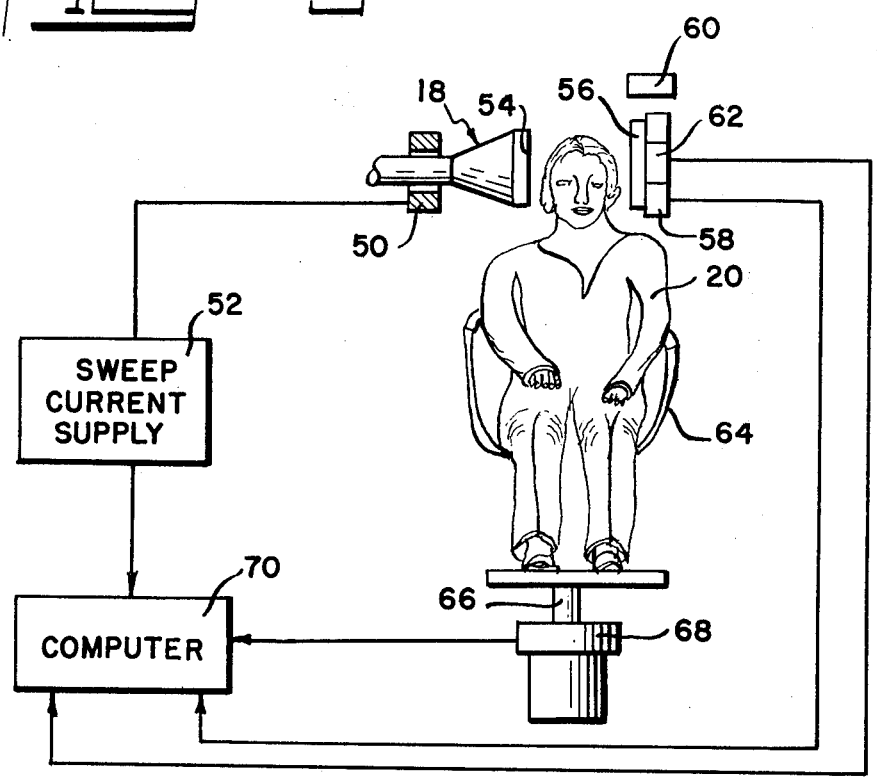
FIG. 3 is a schematic view showing the subject and the sweeping and detection means of FIG. 1.

FIG. 3 is a schematic view of a scanning station. In FIG. 3 sweeping means 18 is disposed near subject 20 to generate a swept beam that will scan the desired portion of subject 20 with a total of the order of $10^8$ protons. Sweeping means 18 includes sweeping coil 50 which is a magnetic coil that operates in a fashion similar to the magnetic sweeping coils of conventional television sets. Sweeping means 18 also includes sweep current supply 52 which applies a predetermined value of current to sweeping coil 50 to generate a sweeping raster. The deflected beam passes through vacuum window 54 and through subject 20 before passing through back absorber 56 to strike back scintillator 58. Back absorber 56 is selected of a material and of a thickness to absorb those protons with energies below a threshold value of energy that is close to the range of selective absorption of the anomaly that is being viewed. Those protons that pass through the subject and through back absorber 56 strike back scintillator 58 and are detected there by photomultiplier 59. Top scintillator 60 and side scintillator 62 are located to provide signals identifying the position of the beam that passes through subject 20. In general, it is not necessary to associate position with the signal from back scintillator 58 and photomultiplier 59 since that position will be known as a function of time from the knowledge of the wave form of sweep current supply 52. Subject 20 may either be fixed in place for the typical exposure which is expected to be of the order of one second or he may be scanned in three dimensions by causing a plurality of beams to traverse the area under investigation while the subject is caused to rotate in those beams. Rotation will be accomplished by affixing the subject to rotating support 64 which is connected by shaft 66 to rotating drive 68. Signals representing appropriate information are coupled from sweep current supply 52, and rotating drive 68 to computer 70 which processes information about beam location, proton count, and subject position to provide a proton radiograph of the subject 20. Information for the three-dimensional radiograph is expected to take approximately 10 proton pulses, each containing about $10^7$ protons, over a time period of the order of 30 seconds.

Back absorber 56 of FIG. 3 has as one function the absorption of protons to remove them from the beam that strikes back scintillator 58 for detection. Thus, the beam that scans subject 20 can be given enough energy to assure that very few protons are absorbed in subject 20, with the attendant increased risk of radiation injury to subject 20. In its simplest form, back absorber 56 is a block of a material that is uniform in thickness. An alternate embodiment of back absorber 56 is shown in FIG. 3a, in which back absorber 56 includes the function of proton detection. In FIG. 3a, back absorber 56 comprises a plurality of scintillators 71 disposed in beam path 72. Each scintillator 71 is coupled optically to a photo-multiplier 73 that generates an electrical signal in response to scintillations in the associated scintillator. Each photomultiplier is connected electrically by a cable 74 to computer 70 for processing of the electrical signals. The embodiment of FIG. 3a allows the scintillator 71 that provides the best image to serve as the primary detector of transmitted protons and extends the range of density variations that can be measured.

Figure 4:
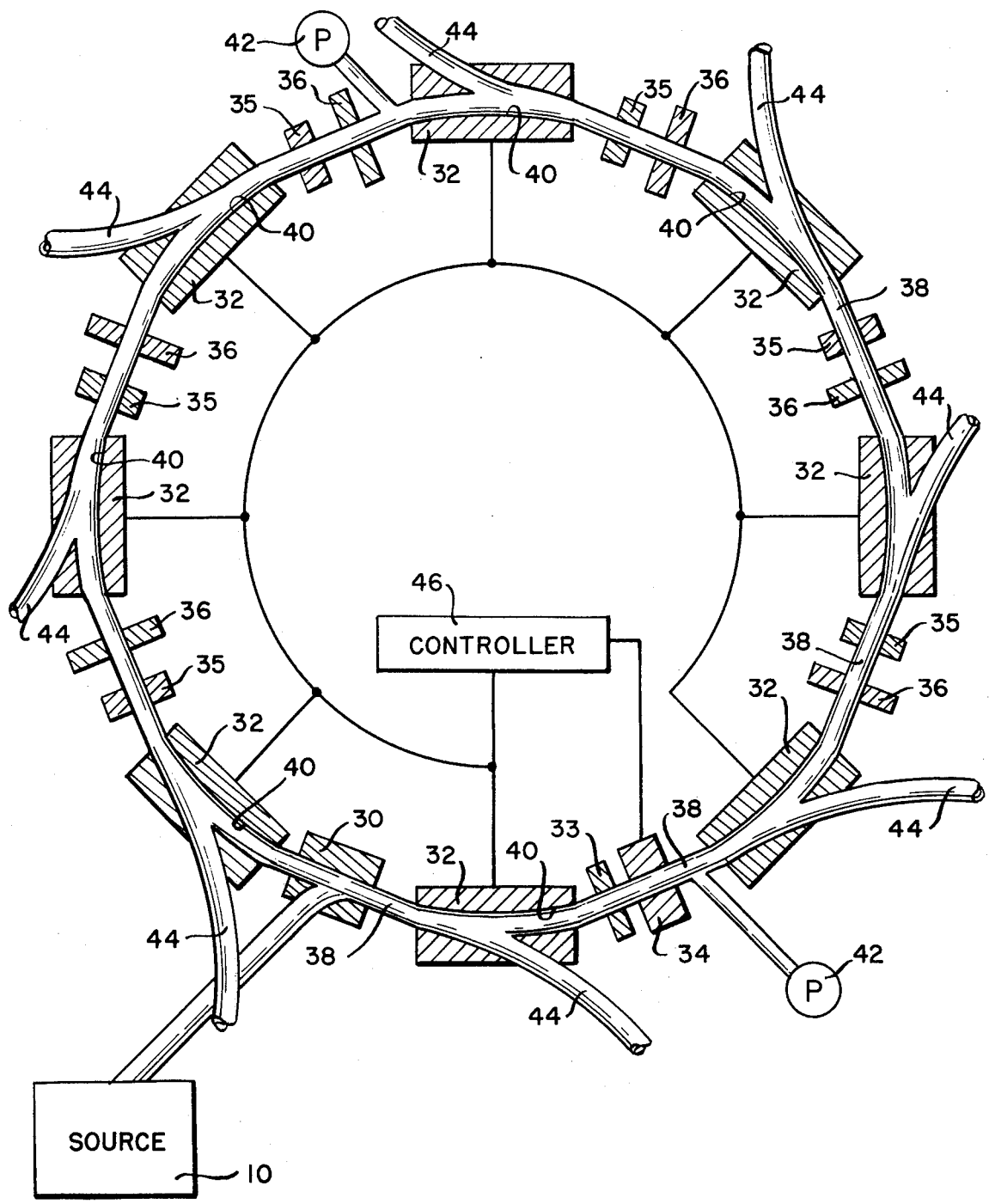
FIG. 4 is an expanded view of the source of negative hydrogen ions of FIG. 1.

FIG. 4 is a schematic diagram and sketch of a generator of negative hydrogen ions for supply and injection into the synchrotron of the present invention. In FIG. 4 discharge voltage source 76 generates an electrical voltage between electrodes 78. Hydrogen from gas source 80 is admitted between electrodes 78 and the gas discharge through the hydrogen generates protons, electrons, and negative hydrogen ions. A negative accelerating electrode 82 attracts the protons and the negative hydrogen ions and electrons are accelerated by the positive accelerating electrode 84 under the influence of the electric field between electrodes 82 and 84 generated by a negative voltage from accelerating voltage source 86. Electrons and negative hydrogen ions pass through aperture 89 into vacuum environment 90 which is the vacuum environment of the accelerator. Many other configurations of generators of negative hydrogen ions are known to exist. Injection bending magnet 92 then directs a magnetic field having components perpendicular to the paths of the negative hydrogen ions and the electrons. The electrons, being lighter, are deflected more than the negative hydrogen ions and are caused to curve into electron absorber 94. The negative hydrogen ions follow beam path 96 for injection into the accelerator. Electron absorber 94 must be designed to prevent the passage of the X-rays that will be generated by impact of electrons in the expected velocity range.

Figure 5:
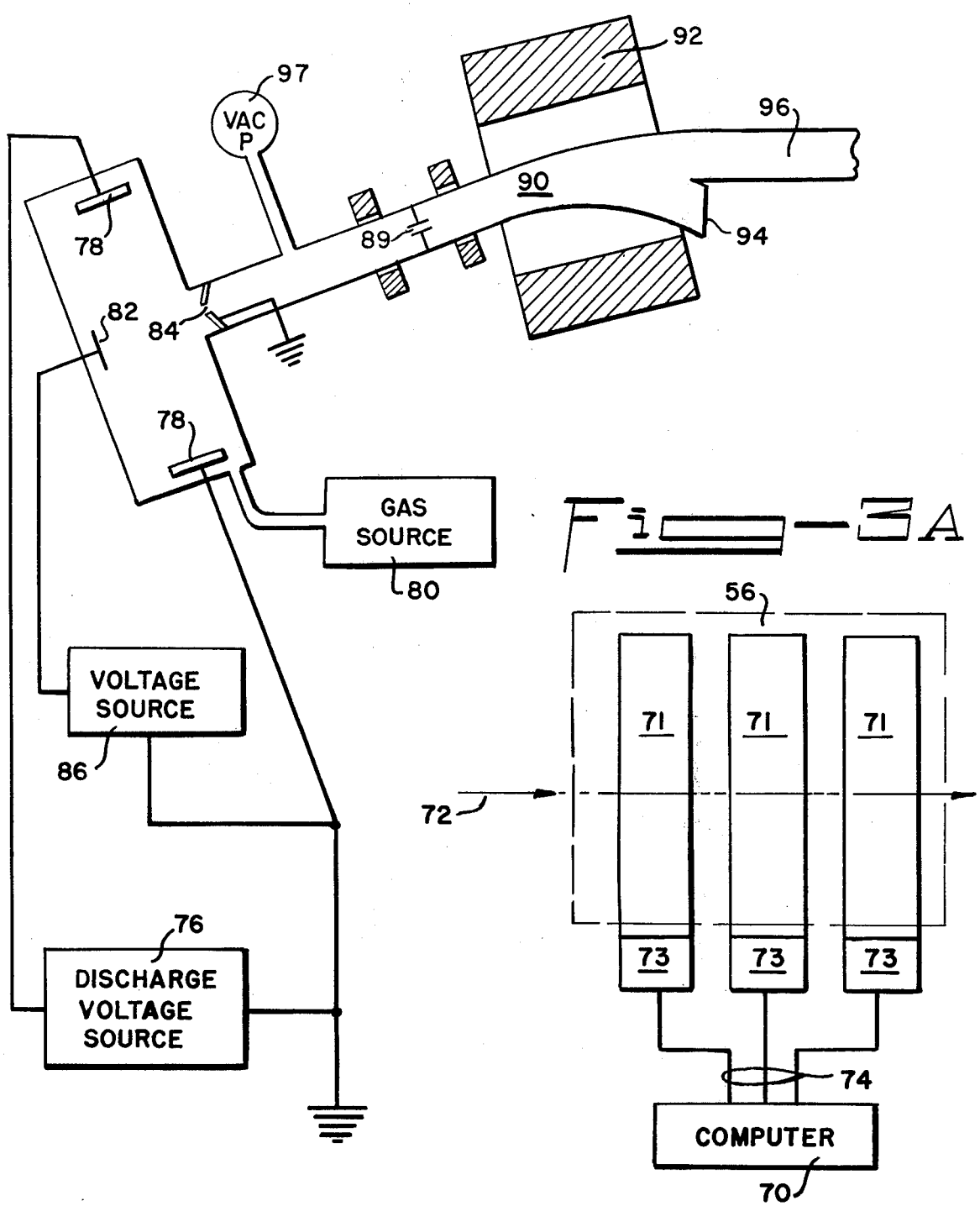
FIG. 5 is a matrix of transmission percentages comprising a radiograph of a sample of human tissue.
Figure 6:
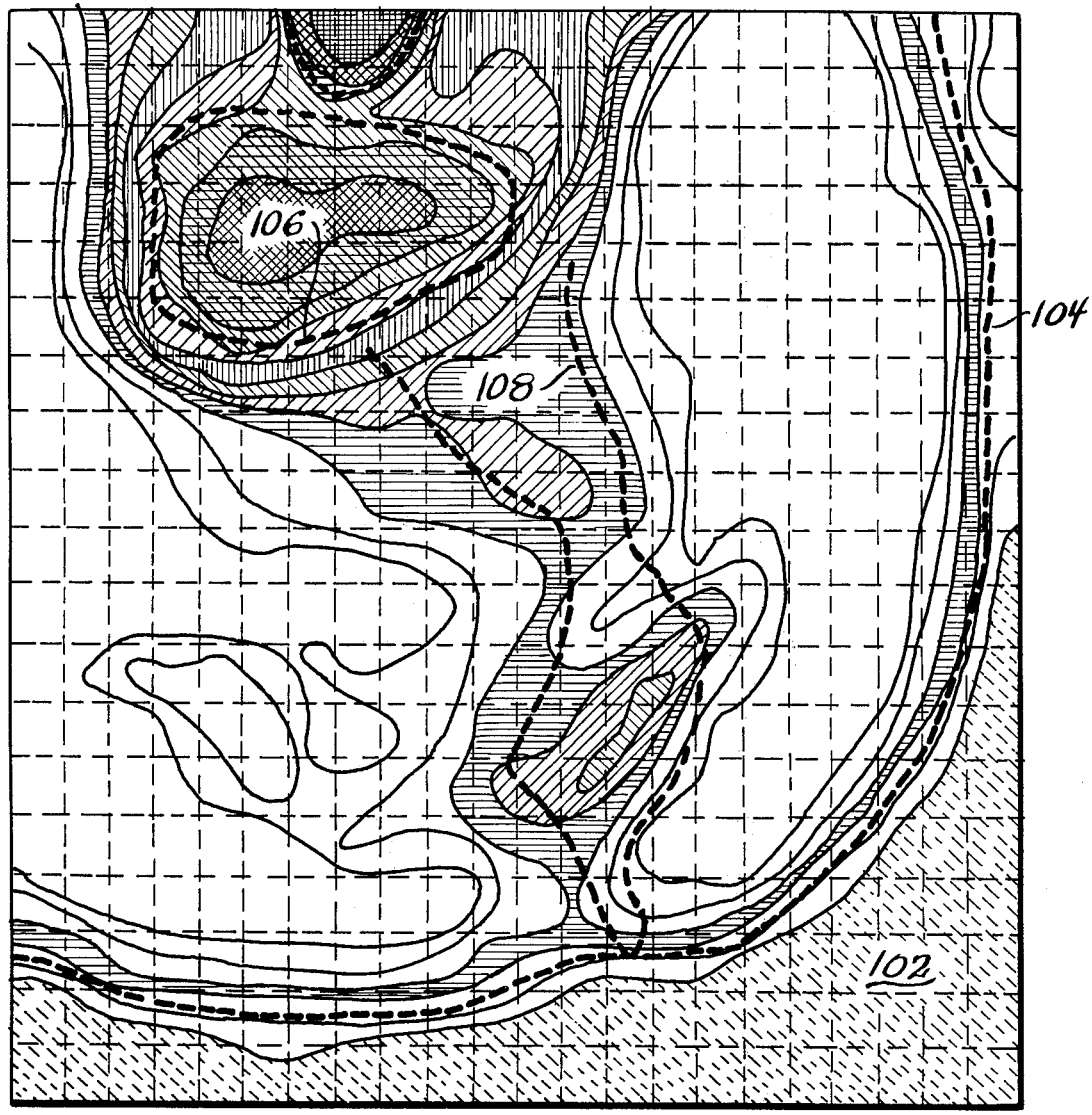
FIG. 6 is a radiograph constructed from the matrix of FIG. 5.

FIGS. 5 and 6 are two presentations of data obtained through the use of a secondary proton beam of the Zero-Gradient Synchrotron at Argonne National Laboratory. FIG. 5 is a matrix of the percent transmission of a ¼-inch proton beam through a specimen of removed human tissue, and FIG. 6 is a radiograph of the proton densities obtained by applying standard relaxation techniques to the percentage figures of FIG. 5. The array of numbers of FIG. 5 was obtained using a single proton detector. The test specimen, a removed human breast containing a tumor, was placed in a water box having parallel sides that were disposed perpendicular to the beam. The purpose of the water box was to assure a substantially constant total thickness of material to be traversed by the proton beam. This demonstrates the sensitivity obtainable by the use of the proton and prevents variations in thickness from distorting the data obtained. The water box described above was indexed a total of 22 steps horizontally and 19 vertically. At each of the positions the specimen was stopped and irradiated with a proton beam, and the percent transmission of protons was determined at that location. The numbers in the array of FIG. 5 are appropriate for entry into and storage in a computer for later reconstruction inao a radiograph such as FIG. 6 for a graphic display of the data determined. In FIG. 6, selected contours from the proton transmission percentages of FIg. 5 are plotted to show the features made apparent in the transmission data. In FIG. 6, region 102 is that part of the water box that contains no part of the specimen. Thus, a region with transmission percentages in the range of 16 to 20 exhibits the same proton transmission as water. Line 104 defines the edge of the specimen which was a removed human female breast containing a tumor. The tumor is distinctly visible in region 106 in which proton transmission percentages are in the range of 8 to 10. The tumor can be located in this one-dimensional proton radiograph by relating it to the location of the mammary duct outlined in region 108.

The proton radiograph shown in FIGS. 5 and 6 epitomizes some of the disadvantages that the present invention is designed to overcome. First, the proton radiograph of FIGS. 5 and 6 was obtained on a large research accelerator that was operated at an energy level and a proton density level below its capacity. The beam used to produce FIGS. 5 and 6 had a diameter of approximately ¼ inch which is much larger than is desirable for effective resolution. That beam was not movable with the equipment at hand, so that it was necessary to index the specimen in a fixed beam in order to obtain the data for reconstruction into a radiograph. The specimen was located in an area that is hazardous to personnel during operation of the equipment because of the radiation levels normally present. It would be impossible to make a proton radiograph of a living human subject on the accelerators at the Zero Gradient Synchrotron without substantial modification of the equipment and serious disruption of normal operation of the accelerator. Radiographs on living human subjects (breast radiographs) have been taken with protons at Harvard using a 160 Mev cyclotron and image intensifiers, and at Berkeley (head) with an 800-Mev alpha beam. Neither accelerator is suitable for hospital use.

It took 3 hours to accumulate the data for the proton radiograph shown in FIG. 6. Subsequent radiographs of removed tissue samples taken at Argonne with 1 mm proton beams from the 200 Mev booster synchrotron required 20 minutes. Neither of the proton beams at Argonne, nor those of any existing proton synchrotron or cyclotron has a beam quality (the product of beam size and divergence angle) suitable for sweeping across a reasonable area of a subject in a period of 1 second. The present invention overcomes this limitation of existing accelerators by using single turn injection of negative hydrogen ions, low beam intensity, and stripping extraction.

The embodiments of the invention in which an exclusive property or privilege is claimed are defined as follows:

1. An apparatus for performing diagnostic proton radiography of a human subject comprising:

a source of negative hydrogen ions;

a synchrotron connected to the source to receive the negative hydrogen ions and accelerate them in an orbit to a precisely controlled predetermined value of energy;

means connected to the synchrotron for stripping the accelerated negative hydrogen ions to produce a beam of protons and extract the beam from the synchrotron;

means for disposing the human subject in the beam of protons;

means for sweeping the beam of protons in a predetermined pattern to traverse a portion of the human subject;

a proton detector disposed to receive the portion of the beam that traverses the human subject and to detect a parameter of the protons received thereat; and display means connected to the sweeping means and the detecting means to produce from information about beam position and beam intensity a proton radiograph of the subject.

2. The apparatus of claim 1 wherein the means for stripping comprise:
   a bumping magnet coupled to the accelerated beam and responsive to a current to change the orbit of the accelerated beam; and
   a fixed foil stripper disposed at the edge of the accelerated beam in a location such that a change in the orbit in response to a current in the bumping magnet moves the beam into contact with the fixed foil stripper to remove electrons from the negative hydrogen ions and convert them to protons.

3. The apparatus of claim 1 wherein the proton detector comprises:
   a beam stop of organic material disposed in the beam that traverses the human subject to absorb all protons below a predetermined value of energy;
   a scintillator disposed in the beam that has traversed the beam stop to detect protons traversing the subject and the beam stop; and
   a photomultiplier coupled optically to the scintillator to generate an electric signal in response to scintillations therein.

4. The apparatus of claim 1 wherein the proton detector comprises:
   a plurality of scintillators disposed sequentially in the beam that has traversed the human subject, and a plurality of photomultipliers each coupled optically to one of said scintillators and generating an electric signal in response to scintillations therein, which electric signal is a function of the parameters of the beam of protons passing through said scintillator.

5. The apparatus of claim 1 wherein the display means comprise:
   a computer to store information about proton count as a function of beam position and means for making a plot of proton count as a function of beam position, which plot is a proton radiograph of the human subject.

6. The apparatus of claim 1 wherein the means for disposing the human subject comprises a fixed support.

7. The apparatus of claim 1 wherein the means for disposing the human subject comprise a rotating support.

8. An apparatus for making proton radiographs of an object comprising:
   a source of negative hydrogen ions;
   a synchrotron connected to the source to receive the negative hydrogen ions and accelerate them in an orbit to a precisely controlled predetermined value of energy of the order of 200 MeV;
   means connected to the synchrotron for stripping the accelerated negative hydrogen ions to produce a beam of protons and extract the beam from the synchrotron;
   means for disposing the object in the beam of protons;
   means for sweeping the beam of protons in a predetermined pattern to traverse a portion of the object;
   means for detecting a parameter of the beam of protons that has traversed the object;
   means for generating a visual display of the parameter as a function of the predetermined pattern, which visual display is a proton radiograph of the object.

9. The apparatus of claim 8 wherein the means for stripping comprise:
   a bumping magnet coupled to the accelerated beam and responsive to a current to change the orbit of the accelerated beam; and
   a fixed foil stripper disposed at the edge of the accelerated beam in a location such that a change in the orbit in response to a current in the bumping magnet moves the beam into contact with the fixed foil stripper to remove electrons from the negative hydrogen ions and convert them to protons.

10. The apparatus of claim 1 wherein the proton detector comprises:
    a plurality of scintillators disposed sequentially in the beam that has traversed the object, and a plurality of photomultipliers each coupled optically to one of said scintillators and generating an electric signal in response to scintillations therein, which electric signal is a function of the parameters of the beam of protons passing through said scintillator.

* * * * *